US008486877B2

(12) United States Patent
Campbell et al.

(10) Patent No.: US 8,486,877 B2
(45) Date of Patent: *Jul. 16, 2013

(54) ALKYLATED HYDROXYAROMATIC COMPOUND SUBSTANTIALLY FREE OF ENDOCRINE DISRUPTIVE CHEMICALS

(75) Inventors: Curtis Bay Campbell, Hercules, CA (US); James J. Harrison, Novato, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 295 days.

This patent is subject to a terminal disclaimer.

(21) Appl. No.: 12/592,007

(22) Filed: Nov. 18, 2009

(65) Prior Publication Data

US 2011/0118160 A1      May 19, 2011

(51) Int. Cl.
*C10M 129/10*   (2006.01)
*C07C 39/06*    (2006.01)
*C07C 15/107*   (2006.01)

(52) U.S. Cl.
USPC ........... 508/584; 568/716; 568/780; 585/446; 585/455; 585/456; 585/463

(58) Field of Classification Search
USPC .................................. 508/584; 568/780, 716
See application file for complete search history.

(56) References Cited

U.S. PATENT DOCUMENTS

| | | |
|---|---|---|
| 3,036,003 A | 5/1962 | Dolton |
| 3,172,892 A | 3/1965 | Le Suer et al. |
| 3,219,666 A | 11/1965 | Norman et al. |
| 3,272,746 A | 9/1966 | Le Suer et al. |
| 3,275,554 A | 9/1966 | Wagenaar |
| 3,329,658 A | 7/1967 | Fields |
| 3,438,757 A | 4/1969 | Honnen et al. |
| 3,449,250 A | 6/1969 | Fields |
| 3,454,555 A | 7/1969 | Vander Voort et al. |
| 3,565,804 A | 2/1971 | Honnen et al. |
| 3,586,629 A | 6/1971 | Otto |
| 3,591,598 A | 7/1971 | Traise et al. |
| 3,666,730 A | 5/1972 | Coleman |
| 3,980,569 A | 9/1976 | Pindar et al. |
| 4,234,435 A | 11/1980 | Meinhardt et al. |
| 4,475,001 A | 10/1984 | Leston |
| 4,612,132 A | 9/1986 | Wollenberg et al. |
| 4,643,838 A | 2/1987 | Liston et al. |
| 4,746,446 A | 5/1988 | Wollenberg et al. |
| 4,873,025 A | 10/1989 | Bolsman |

(Continued)

FOREIGN PATENT DOCUMENTS

| | | |
|---|---|---|
| CZ | 226 912 | 4/1984 |
| EP | 1 548 089 | 6/2005 |
| EP | 1 760 135 | 3/2007 |

*Primary Examiner* — Ellen McAvoy
*Assistant Examiner* — Vishal Vasisth
(74) *Attorney, Agent, or Firm* — Josetta I. Jones; Michael E. Carmen; M. Carmen & Associates

(57) ABSTRACT

An alkylated hydroxyaromatic compound is disclosed which is prepared by reacting at least one hydroxyaromatic compound with at least one branched olefinic propylene oligomer having from about 20 to about 80 carbon atoms in the presence of an acid catalyst, wherein the at least one branched olefinic propylene oligomer is substantially free of any vinylidene content. The alkylated hydroxyaromatic compound has been determined to be substantially free of endocrine disruptive chemicals when the effects were quantified on pubertal development and thyroid function in the intact juvenile female rat.

21 Claims, 2 Drawing Sheets

U.S. PATENT DOCUMENTS

| | | | |
|---|---|---|---|
| 4,912,264 A | 3/1990 | Takeshita et al. | |
| 4,973,764 A | 11/1990 | Oswald et al. | |
| 5,663,457 A | 9/1997 | Kolp | |
| 5,716,912 A | 2/1998 | Harrison et al. | |
| 5,922,922 A | 7/1999 | Harris et al. | |
| 6,153,565 A | 11/2000 | Skinner et al. | |
| 6,165,235 A | 12/2000 | Kolp et al. | |
| 6,191,317 B1 | 2/2001 | Su | |
| 6,281,179 B1 | 8/2001 | Skinner et al. | |
| 6,429,178 B1 | 8/2002 | Skinner et al. | |
| 6,429,179 B1 | 8/2002 | Skinner et al. | |
| 6,440,905 B1 | 8/2002 | Epps et al. | |
| 6,569,818 B2 * | 5/2003 | Nakazato et al. | 508/185 |
| 6,765,106 B2 | 7/2004 | Fenouil et al. | |
| 7,022,763 B2 | 4/2006 | Matsugi et al. | |
| 7,041,864 B2 | 5/2006 | Fung et al. | |
| 7,087,777 B2 | 8/2006 | Fenouil et al. | |
| 7,157,613 B2 | 1/2007 | Arnoldy | |
| 2007/0282143 A1 * | 12/2007 | Driver et al. | 585/24 |
| 2008/0269351 A1 * | 10/2008 | Campbell et al. | 514/731 |

* cited by examiner

ALKYLATED HYDROXYAROMATIC COMPOUND SUBSTANTIALLY FREE OF ENDOCRINE DISRUPTIVE CHEMICALS

BACKGROUND OF THE INVENTION

1. Technical Field

The present invention is directed to an alkylated hydroxyaromatic compound substantially free of endocrine disruptive chemicals and a method of making the alkylated hydroxyaromatic compound.

2. Description of the Related Art

It is well known to catalyze the alkylation of aromatics with a variety of Lewis or Bronsted acid catalysts. Typical commercial catalysts include phosphoric acid/kieselguhr, aluminum halides, boron trifluoride, antimony chloride, stannic chloride, zinc chloride, onium poly(hydrogen fluoride), hydrogen fluoride, solid acid catalysts such as acidic sulfonic acid ion exchange resins, for example Amberlysts®, solid acid clays and acidic zeolitic materials. Alkylation with lower molecular weight olefins, such as propylene, can be carried out in the liquid or vapor phase. For alkylations with higher olefins, such as $C_{16+}$ olefins, the alkylations are done in the liquid phase.

There is increasing evidence that certain synthetic and natural chemicals may act as agonists or antagonists to estrogens or androgens and may interfere in multiple ways with the action of thyroid hormones; such compounds can be called endocrine disruptors. For example, endocrine disruptors can mimic or block chemicals naturally found in the body, thereby altering the body's ability to produce hormones, interfering with the ways hormones travel through the body, and altering the concentration hormones reaching hormone receptors.

Endocrine disruptors and natural estrogens share a common mechanism of action. In normal cases, estrogenic activity is produced by binding natural estrogen to an estrogen receptor (ER) within the nucleus of the cell, followed by transcriptional activation of these occupied ERs. When endocrine disruptors are present, normal estrogenic activity is supplanted when endocrine disruptors bind an ER, causing transcriptional activation of the ER even though no natural estrogen is present. Similarly, antiestrogenic activity is produced by endocrine disruptors which bind to ERs but which do not subsequently activate the occupied ER as well as natural estrogen. Finally, selective estrogen receptor modulators (SERMs) bind to ERs, but subsequently activate cellular responses that differ from those activated by the natural estrogens. In general, all but a very small number of molecules that bind to ERs produce some activation of the receptors, as either estrogens or as SERMs.

Examples of suspected endocrine disruptors may include, for example, Dioxin, Polychlorinated biphenyls (PCBs), Polybromated biphenyls (PBBs), Hexachlorobenzene (HCB), Pentachlorophenol (PCP), 2,4,5-Trichlorophenoxy acetic acid (2,4,5-T), 2,4-Dichlorophenoxyacetic acid (2,4-D), alkylphenols such as Nonylphenol or Octylphenol, Bisphenol A, Di-2-ethylhexyl phthalate (DEHP), butylbenzyl phthalate (BBP), Di-n-butyl phthalate (DBP), Dicylclohexyl phthalate (DCHP), Diethyl phthalate (DEP), Benzo (a) pyrene, 2,4-Dichlorophenol (2,4-DPC), Di(2-ethylhexyl)adipate, Benzophenone, P-Nitrotoluene, 4-Nitrotoluene, Octachlorostyrene, Di-n-pentyl phthalate (DPP), Dihexyl phthalate (DHP), Dipropyl phthalate (DprP), Styrene dimers and trimers, N-Butyl benzene, Estradiol, Diethylhexyl adipate (DEHA), trans-chlorodane, cis-chlorodane, p-(1,1,3,3-Tetramethylbutyl)phenol (TMBP), and (2,4,-Dichlorophenoxy) acetic acid (2,4-PA).

Alkylphenols and products produced by them have come under increased scrutiny due to their association as potential endocrine disruptive components, which is namely due to the weak estrogenic activity of base alkylphenol as well as degradation intermediates of the alkylphenols products. Alkylphenols commercially are used in herbicides, gasoline additives, dyestuffs, polymer additives, surfactants, lubricating oil additives and antioxidants. In the recent years, alkylphenol alkoxylates, such as ethoxylated nonylphenol, have been criticized for having poor biodegradability, high aquatic toxicity of the by-products of the biodegradation of the phenol portion, and there is an increasing concern that these chemicals may act as endocrine disruptors. Some studies have shown that there are links between alkylphenols and declining sperm count in human males and there is evidence that alkylphenols may harmfully disrupt the activity of human estrogen and androgen receptors.

Concern over the environmental and health impact of alkoxylated alkylphenols has led to governmental restriction on the use of these surfactants in Europe, as well as voluntary industrial restrictions in the United States. Many industries have attempted to replace these preferred alkoxylated alkylphenol surfactants with alkoxylated linear and branched alkyl primary and secondary alcohols, but have encountered problems with odor, performance, formulating, and increased costs. The odor and some of the performance difficulties of the alkoxylated alkyl alcohols are related to the residual free alcohol, which is the portion of the reactant alcohol that does not react with alkylene oxide during the alkoxylation step.

U.S. Pat. No. 4,475,001 discloses a process for alkylating phenolic compounds to produce ortho- or para-monoalkylated phenols or 2,4- or 2,6-dialkylated phenols.

U.S. Pat. No. 4,873,025 discloses alkylxylene sulfonate composition prepared by alkylating a para-xylene reactant (or mixture of xylene isomers containing at least about 25 wt % para-xylene), sulfonating the resulting alkylate, and, optionally, converting the product alkylxylene sulfonic acid(s) into the salts. The alkylation may be carried out in a manner known for analogous compounds, e.g., by a Friedel-Crafts reactions using alkyl halide, alkanol, or alkene reactant, in the presence of a Lewis acid catalyst. Preferably the catalyst is hydrogen fluouride or an activated clay.

U.S. Pat. No. 4,912,264 disclose a process for producing hydroxyl-containing alkylated aromatic compounds by the liquid phase reaction of an aromatic compound having at least one hydroxyl group with an alkylating agent in the presence of a heteropoly acid and water.

U.S. Pat. No. 4,973,764 discloses a process for alkylating phenols wherein phenols are alkylated with the olefin component of a thermally cracked sulfur containing petroleum distillate derived from residua in the presence of an acid catalyst to provide monoalkylphenols which have an average of less than two alkyl branches in the said alkyl group.

U.S. Pat. No. 5,922,922 discloses an alkylated aromatic hydrocarbon that is produced having the following properties: (a) less than 40 wt. % of the alkylated aromatic hydrocarbon is 2-aryl; and (b) at least 20 wt. % of the alkylated aromatic hydrocarbon is a monoaklylate.

U.S. Pat. No. 6,765,106 discloses a process for preparing branched olefins comprising 0.5% or less quaternary aliphatic carbon atoms, which process comprises dehydrogenating an isoparaffinic composition over a suitable catalyst which isoparaffinic composition comprises paraffins having a carbon number in the range of from 7 to 35, of which paraffins at least a portion of the molecules is branched, the average number of branches per paraffin molecule being at least 0.7 and the branching comprising methyl and optionally ethyl branches, and which isoparaffinic composition may be obtained by hydrocracking and hydroisomerization of a paraffinic wax.

U.S. Pat. No. 7,022,763 discloses a branched olefin copolymer and a method for making said copolymer. The branched moiety is formed by radical polymerization reaction or anion polymerization reaction.

U.S. Pat. No. 7,041,864 discloses a method for producing linear and/or branched unsaturated product hydrocarbons used ring opening cross-metathesis.

U.S. Pat. No. 7,087,777 discloses a process for preparing branched olefins comprising 0.5% or less quaternary aliphatic carbon atoms, which process comprises dehydrogenating an isoparaffinic composition over a suitable catalyst which isoparaffinic composition comprises paraffins having a carbon number in the range of from 7 to 35, of which paraffins at least a portion of the molecules is branched, the average number of branches per paraffin molecule being at least 0.7 and the branching comprising methyl and optionally ethyl branches, and which isoparaffinic composition may be obtained by hydrocracking and hydroisomerization of a paraffinic wax.

U.S. Pat. No. 7,157,613 discloses a process for producing branched olefins from a mixed linear olefin/paraffin isomerisation feed comprising linear olefins.

Pac et al. Czechoslovakian Patent No. 226,912 ("Pac et al.") disclose a process for alkylating a hydroxyaromatic compound by alkylating a phenol or substituted phenol with a propylene oligomer having a minimum content of 0.25 molar equivalents of vinylidene groups in the course of catalysis of bleaching clay or bleaching clay treated with phosphoric acid or p-toluenesulfonic acid. Pac et al. further disclose that the catalysts used in the process therein are weak alkylation catalyst.

It would be desirable to provide improved alkylated hydroxyaromatic compounds, which are substantially free of endocrine disruptive chemicals.

SUMMARY OF THE INVENTION

In accordance with one embodiment of the present invention, there is provided an alkylated hydroxyaromatic compound prepared by a process comprising reacting at least one hydroxyaromatic compound with at least one branched olefinic propylene oligomer having from about 20 to about 80 carbon atoms in the presence of an acid catalyst, wherein the at least one branched olefinic propylene oligomer is substantially free of any vinylidene content, to provide an alkylated hydroxyaromatic compound, wherein the benzylic carbon attached to the hydroxyaromatic ring is substituted with one group being methyl or a branched alkyl group of 3 to 5 carbon atoms, a second group being a branched alkyl group of at least about 18 carbon atoms having an average of one branch every 2 carbon atoms wherein each branch contains 1 to 2 carbon atoms, and a third group being a linear alkyl group of 1 to 5 carbon atoms, with the proviso that the carbon group directly attached to the benzylic carbon of each of the first and second groups is not a $CH_2$ group.

In accordance with a second embodiment of the present invention, there is provided a process for alkylating an hydroxyaromatic compound comprising reacting at least one hydroxyaromatic compound with at least one branched olefinic propylene oligomer having from about 20 to about 80 carbon atoms in the presence of a acid catalyst, wherein the at least one branched olefinic propylene oligomer is substantially free of any vinylidene content, to provide an alkylated hydroxyaromatic compound wherein the benzylic carbon attached to the hydroxyaromatic ring is substituted with one group being methyl or a branched alkyl group of 3 to 5 carbon atoms, a second group being a branched alkyl group of at least about 18 carbon atoms having an average of one branch every 2 carbon atoms wherein each branch contains 1 to 2 carbon atoms, and a third group being a linear alkyl group of 1 to 5 carbon atoms, with the proviso that the carbon group directly attached to the benzylic carbon of each of the first and second groups is not a $CH_2$ group.

In accordance with a third embodiment of the present invention, there is provided a process for alkylating an hydroxyaromatic compound comprising (a) oligomerizing propylene in the presence of an ionic liquid catalyst to provide at least one branched olefinic propylene oligomer having from about 20 to about 80 carbon atoms, wherein the at least one branched olefinic propylene oligomer is substantially free of any vinylidene content, and (b) reacting at least one hydroxyaromatic compound with the at least one branched olefinic propylene oligomer having from about 20 to about 80 carbon atoms in the presence of an acid catalyst.

In accordance with a fourth embodiment of the present invention, a lubricating oil composition is provided comprising:
(a) a major amount of an oil of lubricating viscosity; and
(b) an alkylated hydroxyaromatic compound prepared by a process comprising: reacting at least one hydroxyaromatic compound with at least one branched olefinic propylene oligomer having from about 20 to about 80 carbon atoms in the presence of a acid catalyst, wherein the at least one branched olefinic propylene oligomer is substantially free of any vinylidene content, wherein the benzylic carbon attached to the hydroxyaromatic ring is substituted with one group being methyl or a branched alkyl group of 3 to 5 carbon atoms, a second group being a branched alkyl group of at least about 18 carbon atoms having an average of one branch every 2 carbon atoms wherein each branch contains 1 to 2 carbon atoms, and a third group being a linear alkyl group of 1 to 5 carbon atoms, with the proviso that the carbon group directly attached to the benzylic carbon of each of the first and second groups is not a $CH_2$ group.

DETAILED DESCRIPTION OF THE PREFERRED EMBODIMENTS

Figure 1:
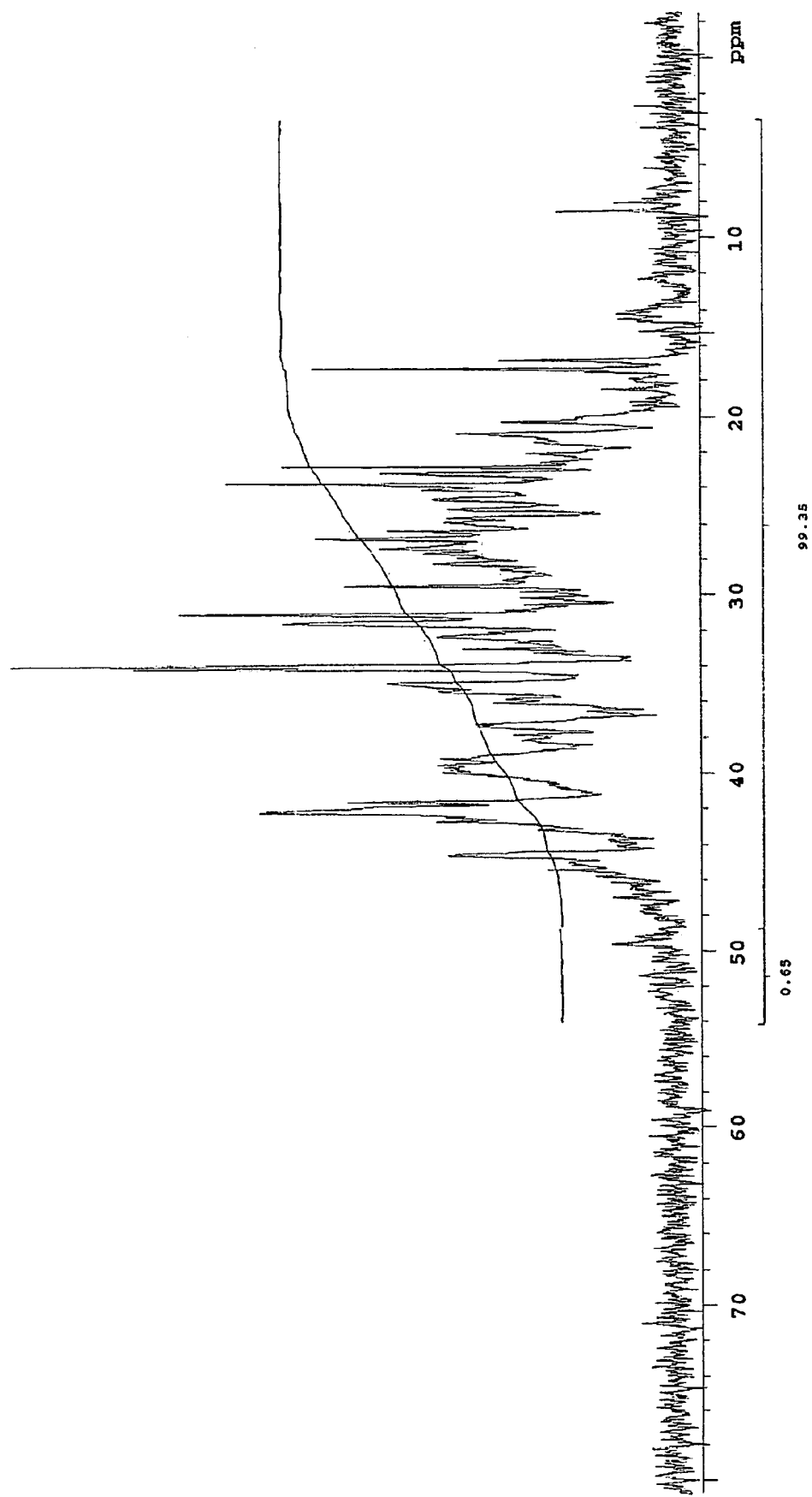
FIG. 1 is a NMR spectra showing the amount of $CH_2$ carbons adjacent to the benzylic carbon atom which is attached to the hydroxyaromatic ring in the product of Example 1.

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

Olefins—The term "olefins" refers to a class of unsaturated aliphatic hydrocarbons having one or more carbon-carbon double bonds, obtained by a number of processes. Those containing one double bond are called mono-alkenes, and those with two double bonds are called dienes, alkyldienes, or diolefins. Alpha olefins are particularly reactive because the double bond is between the first and second carbons. Examples are 1-octene and 1-octadecene, which are used as the starting point for medium-biodegradable surfactants. Linear and branched olefins are also included in the definition of olefins.

Partially Branched Linear Olefins—The term "partially branched linear olefins" refers to a class of linear olefins comprising less than one alkyl branch per straight chain containing the double bond, wherein the alkyl branch may be a methyl group or higher. Partially branched linear olefins may also contain double-bond isomerized olefin.

Branched Olefins—The term "branched olefins" refers to a class of olefins comprising one or more alkyl branches per linear straight chain containing the double bond, wherein the alkyl branch may be a methyl group or higher.

Non-Hydroxyl Containing Aromatic Compounds—The term "non-hydroxyl containing aromatic compounds" refers to aromatic compounds that do not have any hydroxyl groups either on the aromatic ring or on any substituent group(s).

Unsubstituted Aromatic Compounds—The term "unsubstituted compounds" refers to aromatic compounds that do not have any substituents attached to the aromatic ring(s). These compounds may be monocyclic, bicyclic or polycyclic. Examples of such compounds include, but are not limited to, benzene, naphthalene and the like.

Monosubstituted Aromatic Compounds—The term "monosubstituted compounds" refers to aromatic compounds that have one substituent attached to the aromatic ring. These compounds may be monocyclic, bicyclic or polycyclic. Examples of such compounds include, but are not limited to, aromatic compounds with one of the following substituents: —OR, —R, —X, —$NH_2$, —NHR or —$NR_2$ and the like, wherein R is an alkyl group and X is a halide.

Disubstituted Aromatic Compounds—The term "disubstituted compounds" refers to aromatic compounds that have two substituents attached to the aromatic ring(s). The aromatic compounds may be monocyclic, bicyclic or polycyclic. Examples of such compounds include, but are not limited to, aromatic compounds with two substituents selected from the following: —OR, —R, —X, —$NH_2$, —NHR or —$NR_2$ and the like, wherein R is an alkyl group and X is a halide.

Hydroxyaromatic Compound

At least one hydroxyaromatic compound or a mixture of hydroxyaromatic compounds may be used for the alkylation reaction in the present invention. The hydroxyaromatic compounds that may be alkylated in accordance with the process of the present invention include mononuclear monohydroxy and polyhydroxy aromatic hydrocarbons having 1 to 4, and preferably 1 to 3, hydroxyl groups. Suitable hydroxyaromatic compounds include phenol, catechol, resorcinol, hydroquinone, pyrogallol, cresol, and the like and mixtures thereof. In one embodiment, the hydroxyaromatic compound is a phenol.

Sources of Hydroxyaromatic Compound

The at least one hydroxyaromatic compound or the mixture of hydroxyaromatic compounds employed in the present invention is prepared by methods that are well known in the art.

Olefins

Sources of Olefins

The olefins employed in this invention are at least one branched chain olefin derived from the polymerization of propylene. The at least one branched olefinic propylene oligomer may be a mixture of branched olefinic propylene oligomer.

The olefins may also be substituted with other functional groups, such as hydroxy groups, carboxylic acid groups, heteroatoms, and the like, provided that such groups do not react with the acidic ionic liquid catalyst.

The at least one branched olefinic propylene oligomer is selected from propylene oligomers with carbon numbers ranging from about 20 carbon atoms to about 80 carbon atoms. In one embodiment, the at least one branched olefinic propylene oligomer is selected from propylene oligomers with carbon numbers ranging from about 20 to about 60 carbon atoms. In another embodiment, the at least one branched olefinic propylene oligomer is selected from propylene oligomers with carbon numbers ranging from about 20 to about 40 carbon atoms.

In one embodiment, the at least one branched olefinic propylene oligomer is attached to the hydroxyaromatic compound such that the benzylic carbon atom attached to the hydroxaromatic ring is substituted with one group being methyl or a branched alkyl group of 3 to 5 carbon atoms, a second group being a branched alkyl group of at least about 18 carbon atoms having an average of one branch every 2 carbon atoms wherein each branch contains 1 to 2 carbon atoms, and a third group being a linear alkyl group of 1 to 5 carbon atoms, with the proviso that the carbon group directly attached to the benzylic carbon of each of the first and second groups is not a $CH_2$ group.

In general, the at least one branched olefinic propylene oligomer or mixture thereof for use herein is substantially free of any vinylidene content. The term "substantially free" as used herein shall be understood to mean relatively little to no amount of any vinylidene content in the at least one branched olefinic propylene oligomer. In one embodiment, the at least one branched olefinic propylene oligomer has less than about 1 wt. % of vinylidene content.

Preparation of Olefinic Oligomer

The at least one branched olefinic propylene oligomer employed in the present invention is synthesized by oligomerizing propylene in the presence of an ionic liquid catalyst. In one embodiment, the at least one branched olefinic propylene oligomer has a carbon range of from about 20 to about 80.

The at least one branched olefinic propylene oligomer may be prepared by reacting the propylene monomer with the acidic ionic liquid catalyst, as described herein, in a continuous, batch or semi-batch reaction process at from about −20° C. to about 100° C. and a pressure of atmospheric pressure to about 1000 psig. These process conditions are not limiting. Optimization of process conditions in the oligomerization of the olefin is within the purview of one skilled in the art.

Acidic Ionic Liquid Catalyst

The acidic ionic liquid catalyst is composed of two components which form a complex. The first component of the catalyst will typically comprise a compound selected from the group consisting of aluminum halide, alkyl aluminum halide, gallium halide, and alkyl gallium halide. Especially preferred for the first component is aluminum halide or alkyl aluminum halide. In particular, aluminum trichloride may be used as the first component for preparing the catalyst used in practicing the present invention.

The second component making up the ionic liquid catalyst is an organic salt or mixture of salts. These salts may be characterized by the general formula $Q^+A^-$, wherein $Q^+$ is an ammonium, phosphonium, or sulfonium cation and $A^-$ is a negatively charged ion such as $Cl^-$, $Br^-$, $ClO_4^-$, $NO_3^-$, $BF_4^-$, $BCL_4^-$, $PF_6^-$, $SbF_6^-$, $AlCl_4^-$, $ArF_6^-$, $TaF_6^-$, $CuCl_2^-$, $FeCl_3^-$, $SO_3CF_3^-$, $SO_3C_7^-$, and 3-sulfurtrioxyphenyl. In one preferred embodiment, the second component are those quaternary ammonium halides containing one or more alkyl moieties having from about 1 to about 9 carbon atoms such as, for example, trimethylamine hydrochloride, methyltributylammonium, and 1-butylpyridinium, or hydrocarbyl substituted imidazolium halides, such as for example, 1-ethyl-3-methylimidazolium chloride.

The presence of the first component should give the ionic liquid a Lewis acidic character. Generally, the greater the mole ratio of the first component to the second component, the greater the acidity of the ionic liquid mixture. When aluminum trichloride and trimethylamine hydrochloride are used as the first and second components, respectively, of the acidic ionic liquid catalyst, they preferably will be present in a mole ratio of from greater than about 1:1 to about 2:1.

Process for Preparing Alkylated Hydroxyaromatic Compound

In one embodiment of the present invention, the alkylation process is carried out by charging a hydrocarbon feed comprising an hydroxyaromatic compound or a mixture of hydroxyaromatic compounds, at least one branched olefinic propylene oligomer or a mixture of branched olefinic propylene oligomers, and an acid catalyst to a reaction zone in which agitation is maintained. The resulting mixture is held in the alkylation zone under alkylation conditions for a time sufficient to allow substantial conversion (i.e., at least about 70 mole % of the olefin has reacted) of the olefin to hydroxyaromatic alkylate. After the desired time, the reaction mixture is removed from the alkylation zone and fed to a liquid-liquid separator to allow hydrocarbon products to separate from the acid catalyst which may be recycled to the reactor in a closed loop cycle. The hydrocarbon product is further treated to remove excess un-reacted hydroxyaromatic compounds and optionally olefinic compounds from the desired alkylate product. The excess hydroxyaromatic compounds can also be recycled to the reactor.

Many types of reactor configurations may be used for the reactor zone. These include, but are not limited to, batch and continuous stirred tank reactors, reactor riser configurations, ebulating or fixed bed reactors;and other reactor configurations that are well known in the art. Many such reactors are known to those skilled in the art and are suitable for the alkylation reaction. In batch or semi-batch reactors, agitation is critical for the alkylation reaction and can be provided by rotating impellers, with or without baffles, static mixers, kinetic mixing in risers, or any other agitation devices that are well known in the art.

The alkylation process may be carried out at temperatures from about 0° C. to about 200° C. The process is carried out under sufficient pressure that a substantial portion of the feed components remain in the liquid phase. Typically, a pressure of 0 to 150 psig is satisfactory to maintain feed and products in the liquid phase.

The residence time in the reactor is a time that is sufficient to convert a substantial portion of the olefin to alkylate product. The time required is from about 30 seconds to about 300 minutes. A more precise residence time may be determined by those skilled in the art using batch stirred tank reactors to measure the kinetics of the alkylation process.

The at least one hydroxyaromatic compound or mixture thereof and the at least one branched olefinic propylene oligomer or mixture thereof may be injected separately into the reaction zone or may be mixed prior to injection. Both single and multiple reaction zones may be used with the injection of the hydroxyaromatic compounds and the at least one branched olefinic propylene oligomer or mixture thereof into one, several, or all reaction zones. The reaction zones need not be maintained at the same process conditions.

The hydrocarbon feed for the alkylation process may comprise a mixture of hydroxyaromatic compounds and at least one branched olefinic propylene oligomer or mixture thereof in which the molar ratio of hydroxyaromatic compounds to olefins is from about 0.5:1 to about 50:1 or more. In the case where the molar ratio of hydroxyaromatic compounds to olefin is greater than about 1.0, there is an excess amount of hydroxyaromatic compounds present. An excess of hydroxyaromatic compounds is generally used to increase reaction rate and improve product selectivity. When excess hydroxyaromatic compounds are used, the excess un-reacted hydroxyaromatic in the reactor effluent can be separated by, for example, distillation, and recycled to the reactor.

In one embodiment, the alkylation process is a continuous process with closed loop catalyst recycle. A hydrocarbon feed comprising hydroxyaromatic compound(s) or a mixture thereof and at least one branched olefinic propylene oligomer or mixture thereof is charged continuously to a reactor. Alternatively, the hydroxyaromatic compound(s) and mixture of olefin(s) may be charged by separately. At the beginning of the process, an amount of fresh acid catalyst is charged through to the reactor. The hydrocarbon feed and acidic ionic liquid catalyst are maintained in the reactor with agitation under alkylation process conditions for a sufficient time in order for a substantial amount of the at least one branched olefinic propylene oligomer in the feed charge to react and form a hydroxyaromatic alkylate compound.

Pressure in the reactor is maintained by a backpressure valve. The effluent from the reactor is passed through a back-pressure valve to the separator. In the separator, the immiscible hydrocarbon and acid catalyst separate into two phases. As the acid catalyst is more dense than the hydrocarbon phase, the acid catalyst settles to the bottom of the separator. When a sufficient volume of acid catalyst is available to fill line and the bottom of the separator, the flow of fresh catalyst is stopped and "used" or "recycled" catalyst is returned to the reactor from the separator. In this embodiment, the major portion of this process is thus operated under conditions of catalyst recycle, under which no fresh catalyst is added or only a small amount of make-up catalyst is added. The hydrocarbon product stream containing the hydroxyaromatic alkylate compound and excess un-reacted hydroxyaromatic is charged to a product separation section. In product separation, excess hydroxyaromatic compounds are distilled off and returned to the reactor, leaving an alkylated hydroxyaromatic compound.

Acid Catalyst

The alkylated aromatic compound may be prepared using a strong acid catalyst such as a Bronsted or a Lewis acid.

In one embodiment, the strong acid catalyst includes hydrochloric acid, hydrofluoric acid, hydrobromic acid, sulfuric acid, perchloric acid, trifluoromethane sulfonic acid, fluorosulfonic acid, Amberlyst® 36 sulfonic acid, which may be purchased from Rohm and Haas, nitric acid and the like and mixtures thereof. The alkylation process may be carried out in a batch or continuous process. The strong acid catalyst may be recycled or regenerated when used in a batch process or a continuous process.

The strong acid catalyst may be regenerated after it becomes deactivated (i.e., the catalyst has lost all or some portion of its catalytic activity). Methods that are well known in the art may be used to regenerate the deactivated hydrofluoric acid catalyst.

Alkylated Hydroxyaromatic Compound

The resulting product is an alkylated hydroxyaromatic compound having the following structure:

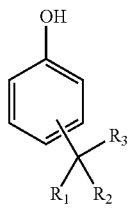

wherein $R_1$ is a branched alkyl group of at least about 18 carbon atoms having an average of at least one branch every 2 carbon atoms wherein each branch contains 1 to 2 carbon atoms, $R_2$ is a methyl or a branched alkyl group having 3 to 5 carbon atoms, and $R_3$ is a linear alkyl group of 1 to 5 carbon atoms, provided that neither $R_1$ nor $R_2$ contain a $CH_2$ adjacent to the benzylic carbon atom which is attached to the hydroxyaromatic ring.

Preferably, the resulting product will be a mixture of ortho and para isomers. Typically, the product will contain about 1 to 99% ortho isomer and 99 to 1% para isomer, and preferably, about 5 to 70% ortho and 95 to 30% para isomer.

Lubricating Oil Composition

Another embodiment of the present invention is directed to a lubricating oil composition containing at least (a) an oil of lubricating viscosity; and (b) an alkylated hydroxyaromatic compound of the present invention which is useful as a lubricating oil additive. The lubricating oil compositions can be prepared by admixing, through conventional techniques, an appropriate amount of the lubricating oil additive of this invention with a base oil of lubricating viscosity. The selection of the particular base oil depends on the contemplated application of the lubricant and the presence of other additives. Generally, the amount of the alkylated hydroxyaromatic compound of this invention in the lubricating oil composition will range from about 0.1 to about 10 wt. %, based on the total weight of the lubricating oil composition.

The oil of lubricating viscosity for use in the lubricating oil compositions of this invention, also referred to as a base oil, is typically present in a major amount, e.g., an amount of greater than 50 wt. %, preferably greater than about 70 wt. %, more preferably from about 80 to about 99.5 wt. % and most preferably from about 80 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered oil of lubricating viscosity used in formulating lubricating oil compositions for any and all such applications, e.g., engine oils, marine cylinder oils, functional fluids such as hydraulic oils, gear oils, transmission fluids, etc. For example, the base oils can be used in formulating lubricating oil compositions for any and all such applications such as passenger car engine oils, heavy duty diesel motor oils and natural gas engine oils. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof, alkylbenzenes such as dodecylbenzenes, tetradecylbenzenes, dinonylbenzenes, di(2-ethylhexyl)-benzenes, and the like, polyphenyls such as biphenyls, terphenyls, alkylated polyphenyls, and the like, alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils includes, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500 to 1000, diethyl ether of polypropylene glycol having a molecular weight of 1,000 to 1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorus containing acids, e.g., tricresyl phosphate, trioctyl phosphate, diethyl ester of decane phosphionic acid, etc., polymeric tetrahydrofurans, and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The lubricating oil compositions of the present invention may also contain other conventional additives for imparting auxiliary functions to give a finished lubricating oil composition in which these additives are dispersed or dissolved. For example, the lubricating oil compositions can be blended with antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. A variety of the additives are known and commercially available. These additives, or their analogous compounds, can be employed for the preparation of the lubricating oil compositions of the invention by the usual blending procedures.

Examples of antioxidants include, but are not limited to, aminic types, e.g., diphenylamine, phenyl-alpha-napthylamine, N,N-di(alkylphenyl)amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic)phenol; and mixtures thereof.

Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 January 1992, see, for example, pages 97-100; aryl phosphates and phosphites, sulfur-containing esters, phosphosulfur compounds, metal or ash-free dithiocarbamates, xanthates, alkyl sulfides and the like and mixtures thereof.

Representative examples of ashless dispersants include, but are not limited to, amines, alcohols, amides, or ester polar moieties attached to the polymer backbones via bridging groups. An ashless dispersant of the present invention may be, for example, selected from oil soluble salts, esters, amino-esters, amides, imides, and oxazolines of long chain hydrocarbon substituted mono and dicarboxylic acids or their anhydrides; thiocarboxylate derivatives of long chain hydrocarbons, long chain aliphatic hydrocarbons having a polyamine attached directly thereto; and Mannich condensation products formed by condensing a long chain substituted phenol with formaldehyde and polyalkylene polyamine.

Carboxylic dispersants are reaction products of carboxylic acylating agents (acids, anhydrides, esters, etc.) comprising at least about 34 and preferably at least about 54 carbon atoms with nitrogen containing compounds (such as amines), organic hydroxy compounds (such as aliphatic compounds including monohydric and polyhydric alcohols, or aromatic compounds including phenols and naphthols), and/or basic inorganic materials. These reaction products include imides, amides, and esters.

Succinimide dispersants are a type of carboxylic dispersant. They are produced by reacting hydrocarbyl-substituted succinic acylating agent with organic hydroxy compounds, or with amines comprising at least one hydrogen atom attached to a nitrogen atom, or with a mixture of the hydroxy compounds and amines. The term "succinic acylating agent" refers to a hydrocarbon-substituted succinic acid or a succinic acid-producing compound, the latter encompasses the acid itself Such materials typically include hydrocarbyl-substituted succinic acids, anhydrides, esters (including half esters) and halides.

Succinic-based dispersants have a wide variety of chemical structures. One class of succinic-based dispersants may be represented by the formula:

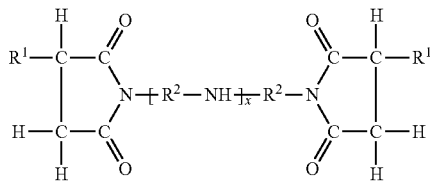

wherein each $R^1$ is independently a hydrocarbyl group, such as a polyolefin-derived group. Typically the hydrocarbyl group is an alkyl group, such as a polyisobutyl group. Alternatively expressed, the $R^1$ groups can contain about 40 to about 500 carbon atoms, and these atoms may be present in aliphatic forms. $R^2$ is an alkylene group, commonly an ethylene ($C_2H_4$) group. Examples of succinimide dispersants include those described in, for example, U.S. Pat. Nos. 3,172,892, 4,234,435 and 6,165,235.

The polyalkenes from which the substituent groups are derived are typically homopolymers and interpolymers of polymerizable olefin monomers of 2 to about 16 carbon atoms, and usually 2 to 6 carbon atoms. The amines which are reacted with the succinic acylating agents to form the carboxylic dispersant composition can be monoamines or polyamines.

Succinimide dispersants are referred to as such since they normally contain nitrogen largely in the form of imide functionality, although the amide functionality may be in the form of amine salts, amides, imidazolines as well as mixtures thereof. To prepare a succinimide dispersant, one or more succinic acid-producing compounds and one or more amines are heated and typically water is removed, optionally in the presence of a substantially inert organic liquid solvent/diluent. The reaction temperature can range from about 80° C. up to the decomposition temperature of the mixture or the product, which typically falls between about 100° C. to about 300° C. Additional details and examples of procedures for preparing the succinimide dispersants of the present invention include those described in, for example, U.S. Pat. Nos. 3,172, 892, 3,219,666, 3,272,746, 4,234,435, 6,165,235 and 6,440, 905.

Suitable ashless dispersants may also include amine dispersants, which are reaction products of relatively high molecular weight aliphatic halides and amines, preferably polyalkylene polyamines. Examples of such amine dispersants include those described in, for example, U.S. Pat. Nos. 3,275,554, 3,438,757, 3,454,555 and 3,565,804.

Suitable ashless dispersants may further include "Mannich dispersants," which are reaction products of alkyl phenols in which the alkyl group contains at least about 30 carbon atoms with aldehydes (especially formaldehyde) and amines (especially polyalkylene polyamines). Examples of such dispersants include those described in, for example, U.S. Pat. Nos. 3,036,003, 3,586,629, 3,591,598 and 3,980,569.

Suitable ashless dispersants may also be post-treated ashless dispersants such as post-treated succinimides, e.g., post-treatment processes involving borate or ethylene carbonate as disclosed in, for example, U.S. Pat. Nos. 4,612,132 and 4,746, 446; and the like as well as other post-treatment processes. The carbonate-treated alkenyl succinimide is a polybutene succinimide derived from polybutenes having a molecular weight of about 450 to about 3000, preferably from about 900 to about 2500, more preferably from about 1300 to about 2400, and most preferably from about 2000 to about 2400, as well as mixtures of these molecular weights. Preferably, it is prepared by reacting, under reactive conditions, a mixture of a polybutene succinic acid derivative, an unsaturated acidic reagent copolymer of an unsaturated acidic reagent and an olefin, and a polyamine, such as disclosed in U.S. Pat. No. 5,716,912, the contents of which are incorporated herein by reference.

Suitable ashless dispersants may also be polymeric, which are interpolymers of oil-solubilizing monomers such as decyl methacrylate, vinyl decyl ether and high molecular weight olefins with monomers containing polar substitutes. Examples of polymeric dispersants include those described in, for example, U.S. Pat. Nos. 3,329,658; 3,449,250 and 3,666,730.

In a preferred embodiment of the present invention, an ashless dispersant for use in the lubricating oil composition is a bis-succinimide derived from a polyisobutenyl group having a number average molecular weight of about 700 to about 2300. The dispersant(s) for use in the lubricating oil compositions of the present invention are preferably non-polymeric (e g., are mono- or bis-succinimides).

Generally, the one or more ashless dispersants are present in the lubricating oil composition in an amount ranging from about 1 to about 8 wt. %, and preferably from about 1.5 to about 6 wt. %, based on the total weight of the lubricating oil composition.

The detergent compounds employed in the lubricating oil composition of the present invention functions both as a detergent to reduce or remove deposits and as an acid neutralizer or rust inhibitor, thereby reducing wear and corrosion and extending engine life. Detergents generally comprise a polar head with long hydrophobic tail, with the polar head comprising a metal salt of an acid organic compound.

The lubricating oil composition according to the present invention may contain one or more detergents, which are normally salts, and especially overbased salts. Overbased salts, or overbased materials, are single phase, homogeneous Newtonian systems characterized by a metal content in excess of that which would be present according to the stoichiometry of the metal and the particular acidic organic compound reacted with the metal. The overbased materials are prepared by reacting an acidic material (typically an inorganic acid or lower carboxylic acid such as carbon dioxide) with a mixture comprising an acidic organic compound, in a reaction medium comprising at least one inert, organic solvent (such as mineral oil, naphtha, toluene, xylene) in the presence of a stoichiometric excess of a metal base and a promoter.

Useful acidic organic compounds for making the overbased compositions include carboxylic acids, sulfonic acids, phosphorus-containing acids, phenols and mixtures thereof Preferably, the acidic organic compounds are carboxylic acids or sulfonic acids and hydrocarbyl-substituted salicylic acids.

Carboxylate detergents, e.g., salicylates, can be prepared by reacting an aromatic carboxylic acid with an appropriate metal compound such as an oxide or hydroxide. Neutral or overbased products may then be obtained by methods well known in the art. The aromatic moiety of the aromatic carboxylic acid can contain one or more heteroatoms such as nitrogen and oxygen. Preferably, the moiety contains only carbon atoms. More preferably, the moiety contains six or more carbon atoms, such as a benzene moiety. The aromatic carboxylic acid may contain one or more aromatic moieties, such as one or more benzene rings, optionally fused together or otherwise connected via alkylene bridges. Representative examples of aromatic carboxylic acids include salicylic acids and sulfurized derivatives thereof such as hydrocarbyl substituted salicylic acid and derivatives thereof. Processes for sulfurizing, for example, a hydrocarbyl-substituted salicylic acid, are known to those skilled in the art. Salicylic acids are typically prepared by carboxylation, for example, by the Kolbe-Schmitt process, of phenoxides. In that case, salicylic acids are generally obtained in a diluent in admixture with an uncarboxylated phenol.

Metal salts of phenols and sulfurized phenols are prepared by reaction with an appropriate metal compound such as an oxide or hydroxide. Neutral or overbased products may be obtained by methods well known in the art. For example, sulfurized phenols may be prepared by reacting a phenol with sulfur or a sulfur-containing compound such as hydrogen sulfide, sulfur monohalide or sulfur dihalide, to form products that are mixtures of compounds in which 2 or more phenols are bridged by sulfur-containing bridges.

The metal compounds useful in making the overbased salts are generally any Group I or Group II metal compounds in the Periodic Table of the Elements. Preferably, the metal compounds are Group II metals and include Group IIa alkaline earth metals (e.g., magnesium, calcium, strontium, barium) as well as Group IIb metals such as zinc or cadmium. Preferably, the Group II metals are magnesium, calcium, barium, or zinc, more preferably magnesium or calcium, and most preferably calcium.

Examples of the overbased detergents include, but are not limited to, calcium sulfonates, calcium phenates, calcium salicylates, calcium stearates and mixtures thereof. Overbased detergents suitable for use in the lubricating oil compositions of the present invention may be low overbased, e.g., an overbased detergent having a BN below about 100. The BN of such a low-overbased detergent may be from about 5 to about 50, or from about 10 to about 30, or from about 15 to about 20. Alternatively, the overbased detergents suitable for use in the lubricating oil compositions of the present invention may be high overbased (e.g., an overbased detergent having a BN above about 100). The BN of such a high-overbased detergent may be from about 100 to about 450, or from about 200 to about 350, or from about 250 to about 280. A low-overbased calcium sulfonate detergent with a BN of about 17 and a high-overbased sulfurized calcium phenate with a BN of about 120 are two exemplary overbased detergents for use in the lubricating oil compositions of the present invention.

The lubricating oil compositions according to the present invention may contain more than one overbased detergent, which may be all low-BN detergents, all high-BN detergents, or a mixture thereof. For example, the lubricating oil compositions of the present invention may contain a first metal-containing detergent which is an overbased alkaline earth metal sulfonate or phenate detergent having a BN of about 100 to about 450 and a second metal-containing detergent which is an overbased alkaline earth metal sulfonate or phenate detergent having a BN of about 10 to about 50.

Suitable detergents for use in the lubricating oil compositions also include "hybrid" detergents such as, for example, phenate/salicylates, sulfonate/phenates, sulfonate/salicylates, sulfonates/phenates/salicylates, and the like. Examples of hybrid detergents include those described in, for example, U.S. Pat. Nos. 6,153,565, 6,281,179, 6,429,178, and 6,429,179.

Generally, the one or more metal-containing detergents are present in the lubricating oil composition in an amount ranging from about 0.5 to about 8.5 wt. %, and preferably from about 1 to about 6 wt. %, based on the total weight of the lubricating oil composition. Where two metal-containing detergents are employed, the first metal-containing detergent is present in the lubricating oil composition in an amount ranging from about 0.5 to about 5 wt. %, and preferably from about 1 to about 3 wt. %, and the second metal-containing detergent is present in the lubricating oil composition in an amount ranging from about 0.1 to about 1.0 wt. %, and preferably from about 0.2 to about 0.5 wt. %, based on the total weight of the lubricating oil composition.

Examples of rust inhibitors include, but are not limited to, nonionic polyoxyalkylene agents, e.g., polyoxyethylene lauryl ether, polyoxyethylene higher alcohol ether, polyoxyethylene nonyiphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof. The amount of the rust inhibitor may vary from about 0.01 wt. % to about 10 wt. %.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine and the like and mixtures thereof The amount of the friction modifier may vary from about 0.01 wt. % to about 10 wt. %.

Examples of antifoaming agents include, but are not limited to, polymers of alkyl methacrylate; polymers of dimethylsilicone and the like and mixtures thereof.

Examples of a pour point depressant include, but are not limited to, polymethacrylates, alkyl acrylate polymers, alkyl methacrylate polymers, di(tetra-paraffin phenol)phthalate, condensates of tetra-paraffin phenol, condensates of a chlorinated paraffin with naphthalene and combinations thereof. In one embodiment, a pour point depressant comprises an ethylene-vinyl acetate copolymer, a condensate of chlorinated paraffin and phenol, polyalkyl styrene and the like and combinations thereof The amount of the pour point depressant may vary from about 0.01 wt. % to about 10 wt. %.

Examples of a demulsifier include, but are not limited to, anionic surfactants (e.g., alkyl-naphthalene sulfonates, alkyl benzene sulfonates and the like), nonionic alkoxylated alkylphenol resins, polymers of alkylene oxides (e.g., polyethylene oxide, polypropylene oxide, block copolymers of ethylene oxide, propylene oxide and the like), esters of oil soluble acids, polyoxyethylene sorbitan ester and the like and combinations thereof. The amount of the demulsifier may vary from about 0.01 wt. % to about 10 wt. %.

Examples of a corrosion inhibitor include, but are not limited to, half esters or amides of dodecylsuccinic acid, phosphate esters, thiophosphates, alkyl imidazolines, sarcosines and the like and combinations thereof. The amount of the corrosion inhibitor may vary from about 0.01 wt. % to about 5 wt. %.

Examples of an extreme pressure agent include, but are not limited to, sulfurized animal or vegetable fats or oils, sulfurized animal or vegetable fatty acid esters, fully or partially esterified esters of trivalent or pentavalent acids of phosphorus, sulfurized olefins, dihydrocarbyl polysulfides, sulfurized Diels-Alder adducts, sulfurized dicyclopentadiene, sulfurized or co-sulfurized mixtures of fatty acid esters and monounsaturated olefins, co-sulfurized blends of fatty acid, fatty acid ester and alpha-olefin, functionally-substituted dihydrocarbyl polysulfides, thia-aldehydes, thia-ketones, epithio compounds, sulfur-containing acetal derivatives, co-sulfurized blends of terpene and acyclic olefins, and polysulfide olefin products, amine salts of phosphoric acid esters or thiophosphoric acid esters and the like and combinations thereof The amount of the extreme pressure agent may vary from about 0.01 wt. % to about 5 wt. %.

In another embodiment of the invention, the one or more alkylated hydroxyaromatic compounds of the present invention may be provided as an additive package or concentrate in which the one or more of the alkylated hydroxyaromatic compounds are incorporated into a substantially inert, normally liquid organic diluent such as, for example, mineral oil, naphtha, benzene, toluene or xylene to form an additive concentrate. These concentrates usually contain from about 20% to about 80% by weight of such diluent. Typically a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. The additive package will also typically contain one or more of the various other additives, referred to above, in the desired amounts and ratios to facilitate direct combination with the requisite amount of base oil.

The applications to which the lubricating oil compositions of this invention may be put are not particularly limited, and include e.g. marine cylinder lubricants, trunk piston engine oils, and system oils; automotive engine oils; railroad engine oils; stationary engine oils such as natural gas engine oils; greases; and functional fluids such as tractor hydraulic fluids, gear oils, antiwear hydraulic oils, and transmission fluids.

The following examples are presented to illustrate specific embodiments of this invention and are not to be construed in any way as limiting the scope of the invention.

EXAMPLE 1A

Preparation of Trimethylammonium Chloroaluminate Ionic Liquid Catalyst

To a 1000 ml, dry, three neck glass round bottom flask fitted with a mechanical stirrer, thermometer and water cooled reflux condenser was added 67.2 grams (0.7 moles) of trimethylammonium hydrochloride. This was heated to 105° C. under vacuum (400 mm Hg) for about 65 hours and then allowed to cool to room temperature under a nitrogen atmosphere. To the hydrochloride salt was added 187.8 (1.4 moles) of aluminum trichloride in several portions under nitrogen over about 30 minutes with stirring while the temperature of the contents of the flask increased to 103° C. The reaction was then heated to about 70° C. and stirred for 2 hours and 10 minutes and then cooled to room temperature under nitrogen. The liquid trimethylammonium chloroaluminate ionic liquid was kept under nitrogen until use.

EXAMPLE 1B

Oligomerization of Propylene with Ionic Liquid Catalyst in a Continuously Stirred Flow Reactor To a clean, dry, approximately 1 liter, jacketed glass reactor connected to an external chiller/heater and equipped with a bottom drain valve and fitted with a mechanical paddle stirrer, thermometer, fitted glass inlet at the bottom of the reactor and a water cooled condenser fitted with a rubber serum stopper and a hypodermic needle vent was added approximately 195 grams of the ionic liquid catalyst of Example 1A and approximately 150 ml of hexane. The stirrer was turned on at high speed and the external chiller/heater was set to 55° C. Propylene gas was introduced through the gas dispersion tube at 0.2-0.4 liters/minute for approximately 8 hours while the reactor temperature varied between 55° C. and 61° C.

At the end of this 8 hour time period, the stirrer and propylene gas addition was stopped and the ionic liquid catalyst was drained from the reactor followed by the hexane layer. Two days later, the collected ionic liquid catalyst was recharged to the reactor followed by 150 ml of hexane. The external heater/chiller was set to 55° C. and propylene gas was introduced through the gas dispersion tube at 0.2-0.4 liters/minute for 30.5 hours while the reactor temperature varied between 55° C. and 58° C. The stirrer was then stopped, the catalyst drained from the reactor followed by the hexane layer. The combined hexane layers were quenched with poured onto ice and washed with water, dried over anhydrous magnesium sulfate, filtered and the hexane removed under vacuum (1 mm Hg vacuum) at 80° C. using a rotoevaporator to yield 450 grams of a first product. Analysis of the first product by SFC indicated a broad molecular weight distribution and analysis by HPLC Size Exclusion Chromatography using MALS detection showed a Mn=935, Mw=1013 and a DI of 1.08.

The above procedure was repeated using 200 grams of ionic liquid catalyst, 150 grams of hexane and propylene gas addition over a combined time of approximately 53 hours at a reactor temperature between 55° C. and 61° C. without stopping the reaction (an additional 100 ml of hexane was added to the reactor after approximately 45 hours of reaction time). Workup and removal of the hexane solvent afforded 460 grams of a second product. Analysis of this second product by SFC indicated a broad molecular weight distribution and analysis by HPLC Size Exclusion Chromatography using MALS detection showed a Mn=1321, Mw=1348 and a DI of 1.02.

The first product and second product were combined and analyzed by carbon NMR and found to contain 0.0014% methylvinylidene olefin.

EXAMPLE 1

Preparation of Propylene Oligomer Alkylphenol

A 2-liter glass, 4-neck, round bottom flask fitted with a mechanical stirrer, water condenser, liquid addition funnel and thermometer was charged with 268.9 gm (2.86 moles) of phenol under a nitrogen atmosphere. The temperature of the reaction was raised to 130° C. with agitation and approximately 6.7 gm of trifluoromethane sulfonic acid was added dropwise via syringe (the reaction mixture turned an orange color) followed immediately by 787 gm (approximately 0.95 moles) of the propylene oligomer of Example 1B via an the addition funnel. The reaction mixture was held at 130° C. for 2 hours and then cooled to room temperature, diluted with 1 liter of hexane and washed with aqueous saturated sodium bicarbonate solution. The organic layer was dried over anhydrous magnesium sulfate, gravity filtered and the solvent removed under vacuum with to afford 806 gm of a brown oil. A portion (775 gm) of this brown oil was fractionally vacuum distilled (10"×2" unpacked Vigreux column at 1.0 Torr and temperature programmed from 151 to 204° C.) to remove any remaining unreacted phenol and yielded 725 gm of a second brown oil. A portion of this second brown oil (575 gm) was fractionally vacuum distilled a second time (10"×2" unpacked Vigreux column at 0.3 Torr and temperature programmed from 193 to 240° C.) to remove any $C_2$-$C_{18}$ alkylphenol and afforded the purified propylene oligomer alkylphenol:

1H NMR, 0.3-2.0 ppm (aliphatic C—H), 4-5 ppm (O—H) and 6.6-7.6 ppm (aromatic C—H); IR 745 cm-1 (ortho-alkylphenol), 825 cm-1 (para-alkylphenol); HPLC (5 cm×4.6 cm 5µ C8 Column, 78:22 methanol: water 10 minutes then 85/15 100% Methanol for 35 minutes at 1 ml/min, 2 microliter injection using a Fluorescence 225×313 em) showed 0.02 weight % $C_2$-$C_{18}$ alkylphenol present; Adsorption chromatography (Silica Gel SepPak®, hexane, then di-ethylether) showed the propylene oligomer alkylphenol to contain 70.0 weight % alkyphenol with the remainder being unreacted polypropylene oligomer.

Determination of the Absence of a $CH_2$ Adjacent to the Benzylic Carbon Atom Which is Attached to the Hydroxy Aromatic Ring for the Product of Example 1

A $CH_2$ adjacent to the benzylic carbon atom which is attached to the hydroxyaromatic ring is calculated to appear at about 49 to 51 ppm in the carbon NMR spectrum. This chemical shift (50.5 ppm) is unique for $CH_2$ carbons in the structure:

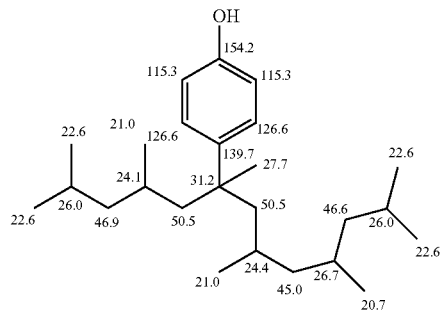 [SMILES: CC(C)CC(C)CC(C)CC(C)(CC(C)CC(C)C)c1ccc(O)cc1]

This calculation was determined by using the software Chem-Draw Ultra®, ©1985-2001, version 7.0.1, CambridgeSoft Corporation, 100 CambridgePark Drive, Cambridge, Mass. 02140 USA.

Distortionless Enhancement of Polarization Transfer (DEPT) NMR was carried out in order to determine the total amount of $CH_2$ that was adjacent to the benzylic carbon atom which is attached to the hydroxyaromatic ring in the product of Example 1. DEPT was first described in Doddrell et al., *J. Magn. Reson.* 48:323 (1982) and is available on most NMR instruments. The DEPT experiment gives four separate NMR spectra for a sample which includes: (a) all protonated carbons, (b) CH carbons, (c) $CH_2$ carbons, and (d) $CH_3$ carbons. FIG. 1 shows only the amount of $CH_2$ carbons from the DEPT experiment in the product of Example 1.

The integration of the region from about 49 to 51 ppm in FIG. 1 shows that only about 0.65% of the $CH_2$ carbons in the product from Example 1 are adjacent to the benzylic carbon atom which is attached to the hydroxyaromatic ring. This means that greater than 99% of the $CH_2$ carbons in the product from Example 1 are not adjacent to the benzylic carbon atom which is attached to the hydroxyaromatic ring.

COMPARATIVE EXAMPLE A

Purified Propylene Tetramer Alkylphenol Calcium Salt

Branched dodecyl phenol calcium salt was prepared from the alkylation of phenol with a mixture of branched chain $C_{10}$-$C_{15}$ olefin derived primarily from propylene tetramer and the resulting alkylphenol had the following carbon distribution set forth below in Table 1:

TABLE 1

| Carbon Number | Wt. % |
| --- | --- |
| ≦$C_9$ | 0 |
| $C_{10,11}$ | 6.6 |
| $C_{12}$ | 82.7 |
| $C_{13+}$ | 10.7 |

To a 5 neck, 3 liter round bottom flask equipped with a mechanical stirrer, Dean Stark trap fitted with a condenser under an atmosphere of dry nitrogen was charged 607 gm (2.32 moles) of the above $C_{12}$ branched alkylphenol followed by 500 gm of Chevron RLOP 100N oil. This mixture was heated to approximately 150° C. and maintained at this temperature overnight with stirring. The mixture was then cooled to approximately 20° C. using an ice bath and 48.8 gm (1.16 moles) of calcium hydride ($CaH_2$, 98% obtained from Aldrich Chemical Company) was added to the mixture in approximately 10 gram portions with stirring. The mixture was then heated to approximately 270° C. in approximately 1 hour and held at this temperature with stirring for 8 hours. The mixture was then cooled to 200° C. overnight and then raised the temperature to 280° C. and held there for 4 hours. The mixture was then cooled to 230° C. and maintained at this temperature overnight. The mixture was then cooled to approximately 150° C. and filtered through a sintered glass Buchner funnel containing Celite® filter aid (dried overnight at 120° C.) into a dry filter flask with the aid of vacuum over approximately 3.5 hours. The resulting light honey colored liquid contained 3.82% calcium. This reaction was repeated and the combined products were a honey colored liquid containing 3.82% calcium.

COMPARATIVE EXAMPLE B

Propylene Pentamer Alkylphenol Calcium Salt

Branched pentadecylphenol calcium salt was prepared from the alkylation of phenol with a branched chain $C_{14}$-$C_{18}$ olefin derived primarily from propylene pentamer. To a 2-liter round bottom flask equipped with a mechanical stirred, Dean Stark trap fitted with a condenser under an atmosphere of dry nitrogen was charged with 705 gm (2.32 moles) of a $C_{15}$ branched alkylphenol followed by 500 gm of Chevron RLOP 100N oil. This mixture was cooled to approximately 13° C. using an ice bath and then 48.8 gm (1.16 moles) of calcium hydride (98% obtained from Aldrich Chemical Company) was added in approximately 10 gm portions with stirring. The reaction was then heated to 100° C. over 50 minutes and then heated to 200° C. for over 140 minutes and held at 200° C. for approximately 18 hours and then heated to 280° C. over 1 hour and held at 280° C. for 8.5 hours and then cooled to 230° C. and held at 230° C. for approximately 14 hours. The reaction was then cooled to 150° C. and filtered through a dry, hot (150° C.) 600 mL Buchner funnel containing a filter bed of Celite and maintained between 110° C. and 120° C. with the aid of a vacuum to afford a product containing 3.51 wt % calcium.

COMPARATIVE EXAMPLE C

Propylene Tetramer Alkylphenol

Branched, principally, $C_{12}$ or branched dodecyl phenol, was prepared from the alkylation of phenol with a branched chain $C_{10}$-$C_{15}$ olefin derived from propylene tetramer. The resulting alkylphenol had the following carbon distribution set forth below in Table 2:

TABLE 2

| Carbon Number | Wt. % |
|---|---|
| $\leq C_{10}$ | 1 |
| $C_{11}$ | 18 |
| $C_{12}$ | 59 |
| $C_{13}$ | 17 |
| $C_{14}$ | 4 |
| $\geq C_{15}$ | 1 |

COMPARATIVE EXAMPLE D

Propylene Tetramer Dimer Alkylphenol

A glass, three-neck, round bottom flask fitted with a mechanical stirrer, water condenser and thermometer was charged with 896 gm (~2.7 moles) of propylene tetramer dimer and 82.4 gm of Amberlyst® 36 sulfonic acid ion exchange resin. This mixture was heated to 90° C. with stirring and then 753 gm (8.0 moles) of phenol was charged to the reactor. The temperature of the reaction was increased to 120° C. and held for 24 hours. The temperature of the reaction was then increased to 130° C. for 1.5 hours and then allowed to cool to room temperature. The reaction mixture was then filtered with the aid of vacuum through a glass fritted Buchner funnel. The resulting filtrate (1721 gm) was fractionally vacuum distilled (10"×2" Vigreux column, 10-50 Torr, temperature programmed from 111 to 180° C.) to remove unreacted phenol and afforded 1079 gm a bottoms product. The above alkylation reaction was repeated and the combined distilled bottoms product (1721 gm) were fractionally vacuum distilled a second time (10"×2" Vigreux column, 1.0 Torr, temperature programmed from 100 to 195° C.) to remove any $C_2$-$C_{18}$ alkylphenol and afforded 675 gm of the purified propylene tetramer dimer alkylphenol:

IR 745 cm-1 (ortho-alkylphenol), 825 cm-1 (para-alkylphenol); FIMS analysis showed the presence of $C_{10}$-$C_{31}$ alkylphenols; HPLC (5 cm×4.6 cm 5μ C8 Column, 78:22 methanol: water 10 minutes then 85/15 100% Methanol for 35 minutes at 1 ml/min, 2 microliter injection using a Fluorescence 225×313 em) showed 3.05 weight % $C_2$-$C_{18}$ alkylphenol present; Adsorption chromatography (Silica Gel Sep-Pak®, hexane, then di-ethylether) showed the propylene tetramer dimer alkylphenol contained 88.0 weight % alkylphenol with the remainder being unreacted polypropylene tetramer dimer.

Assessment

Assessment of Pubertal Development in Juvenile Female CD® (Sprague-Dawley) Rats was carried out after exposure to the compounds of Example 1 and Comparative Examples A-D, administered by oral gavage. This assessment is a modified version of the toxicology screen referred to as the "female pubertal assay." This assay detects estrogenic and anti-estrogenic activity as well as perturbations to the hypothalamic-pituitary-gonadal/thyroidal axis during the course of twenty days of test substance administration. Effects are detected via changes to the timing of sexual maturation (age at vaginal opening), changes to organ weights, and age at first estrus. This assay is designed to be sensitive to endocrine endpoints, but is an apical design from the perspective that it cannot single out one particular endocrine-mediated mechanism.

It should be noted that the female pubertal assay is an apical assay that may detect chemicals with biological activity upon the hypothalamic-pituitary-gonadal/thyroidal axes. Chemicals what act directly upon the female gonads, such as those described as estrogen mimics, would also be detected in a simpler assay known as the uterotrophic assay. The uterotrophic assay is specific for estrogenicity. However, the female pubertal assay should detect both chemicals that act directly upon the female gonads as well as chemicals that act upon other components in these endocrine axes.

Briefly, the assay is conducted as follows. Suitable female rats, 21 days of age, within the weight range were weaned and randomized into four treatment groups. Each treatment group consisted of fifteen females. Dosage levels were determined and dose volumes were based on daily body weight. Animals were orally dosed with a test compound or the vehicle (Mazola® corn oil) beginning on day 22 and continuing through 41 days of age. A separate vehicle control group dosed with corn oil was run concurrently with each component. Clinical signs were observed twice daily during the experimental period with body weights recorded daily. Beginning with postnatal day "PND" PND 25, animals were examined for vaginal perforation. The day of complete vaginal perforation was identified as the age of vaginal opening, and body weight was recorded on that day. Daily vaginal smears to determine the stage of estrus were performed beginning on the day of vaginal perforation until necropsy. At necropsy on PND 42, females were euthanized and blood was collected from the vena cava for analysis of Thyroid Stimulating Hormone (TSH) and Thyrroxine ($T_4$). Uterine, ovary, liver, pituitary, kidney, thyroid and adrenal weights were collected. Body weights, body weight gains, organ weights (wet and blotted) luminal fluid weights, mean day of acquisition of vaginal perforation, mean age of first estrous and estrous cycle length was analyzed using statistical methods, such as by a parametric one-way analysis of variance, (ANOVA) to determine intergroup differences.

TABLE 3

Vaginal Opening and Body Weight of Treated Females

| Compound | Dose (mg/kg/day) | Days to Vaginal Opening | Body weight at Sexual Maturation |
|---|---|---|---|
| Example 1 | 0 | 32.1 | 111.4 |
|  | 60 | 32.5 | 112.4 |
|  | 250 | 32.5 | 112.2 |
|  | 1000 | 31.1 | 103.4 |
| Comparative Example A | 0 | 34.5 | 105.9 |
|  | 60 | 28.3 | 104.4 |
|  | 250 | 27.9 | 96.0 |
|  | 1000 | 27.6 | 74.6 |
| Comparative Example B | 0 | 33.2 | 110.9 |
|  | 60 | 29.6 | 89.7 |
|  | 250 | 26.5 | 75.2 |
|  | 1000 | 27.9 | 77.4 |
| Comparative Example C | 0 | 32.5 | 111.9 |
|  | 10 | 33.3 | 113.5 |
|  | 50 | 28.3 | 85.4 |
|  | 200 | 28.2 | 83.4 |
|  | 800 | 28.9 | 73.9 |
| Comparative Example D | 0 | 32.7 | 109.7 |
|  | 60 | 31.7 | 98.5 |
|  | 250 | 26.9 | 73.9 |
|  | 1000 | 26.5 | 71.9 |

The data in Table 3 demonstrate sensitivity of the assay to differentiate among the compounds in capability to disrupt endocrine function as measured by sexual maturation.

Figure 2:
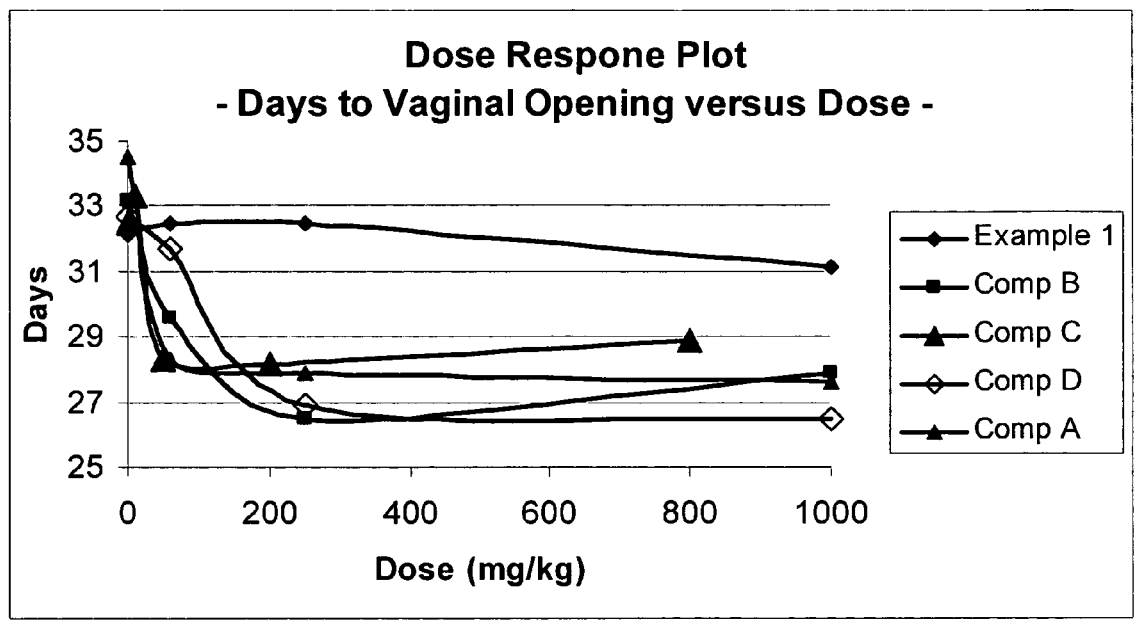
FIG. 2 is a dose response plot to assess pubertal development in juvenile female rats. The data in FIG. 2 demonstrate sensitivity of the assay to differentiate among the compounds tested in capability to disrupt endocrine function as measured by sexual maturation.

Example 1, even at very high dosages, showed no evidence of endocrine disruption as measured by a decrease in days to vaginal opening (See Table 3 and FIG. 2) or decrease in body weight at sexual maturation. (See Table 3). By comparison, Comparative Examples A, B, C and D showed evidence of endocrine disruption. In addition, the Comparative Examples A, B, C and D exhibited a decreasing trend in body weight, with a significant effect at high dose rates, similar decreasing trends were also noted for regarding the average postnatal day of vaginal opening. It should also be noted that potency does not vary greatly between the free alkylphenol and the calcium salt (See Comparative Examples A and C).

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. An alkylated hydroxyaromatic compound prepared by a process comprising:
reacting at least one hydroxyaromatic compound with at least one branched olefinic propylene oligomer having from about 20 to about 80 carbon atoms in the presence of an acid catalyst, wherein the at least one branched olefinic propylene oligomer has less than about 1 wt. % of vinylidene content, to provide an alkylated hydroxyaromatic compound. wherein the benzylic carbon attached to the hydroxyaromatic ring is substituted with one group being methyl or a branched alkyl group of 3 to 5 carbon atoms, a second group being a branched alkyl group of at least about 18 carbon atoms having an average of one branch every 2 carbon atoms wherein each branch contains 1 to 2 carbon atoms, and a third group being a linear alkyl group of 1 to 5 carbon atoms, with the proviso that the carbon group directly attached to the benzylic carbon of each of the first and second groups is not a $CH_2$ group.

2. The alkylated hydroxyanmatic compound prepared by the process of claim 1, wherein the at least one hydroxyaromatic compound is a mononuclear hydroxyaromatic hydrocarbon having from about 1 to about 4 hydroxyl groups.

3. The alkylated hydroxyaromatic compound prepared by the process of claim 2, wherein the at least one hydroxyaromatic compound is a mononuclear hydroxyaromatic hydrocarbon having from about 1 to about 3 hydroxyl groups.

4. The alkylated hydroxyaromatic compound prepared by the process of claim 3, wherein the at least one hydroxyaromatic compound is phenol.

5. The alkylated hydroxyaromatic compound prepared the process of claim 1, wherein the acid catalyst is a strong acid.

6. The alkylated hydroxyaromatic compound prepared by the process of claim 1, wherein the acid catalyst is trifluoromethane sulfonic acid or an acidic sulfonic acid ion exchange resin.

7. The alkylated hydroxyaromatic compound prepared by the process of claim 1, wherein the at least one branched olefinic propylene oligomer has from about 20 to about 60 carbon atoms.

8. The alkylated hydroxyaromatic compound prepared by the process of claim 1, wherein the at least one branched olefinic propylene oligomer is a mixture of branched olefinic propylene oligomers.

9. A lubricating oil composition comprising;
(a) a major amount of an oil of lubricating viscosity; and
(b) one or more of the alkylated hydroxyaromatic compounds of claim 1.

10. The lubricating oil composition of claim 9, wherein the one or more alkylated hydroxyaromatic compounds is present in an amount of about 0.1 wt. % to about 10 wt. %, based on the total weight of the composition.

11. The lubricating oil composition of claim 9, further comprising at least one additive selected from the group consisting of an antioxidant, anti-wear agent, detergent, rust inhibitor, dehazing agent, demulsifying agent, metal deactivating agent, friction modifier, pour point depressant, antifoaming agent, co-solvent, package compatibiliser, corrosion-inhibitor, ashless dispersant, dye, extreme pressure agent and mixtures thereof.

12. A process for alkylating a hydroxyaromafic compound comprising reacting at least one hydroxyaromatic compound with at least one branched olefinic propylene oligomer having from about 20 to about 80 carbon atoms in the presence of an acid catalyst, wherein the at least one branched olefinic propylene oligomer has less than about 1 wt. % of vinylidene content to provide an alkylated hydroxyaromatic compound, wherein the benzylic carbon attached to the hydroxyaromatic ring is substituted with one group being methyl or a branched alkyl group of 3 to 5 carbon atoms, a second group being a branched alkyl group of at least about 18 carbon atoms having an average of one branch every 2 carbon atoms wherein each branch contains 1 to 2 carbon atoms, and a third group being a linear alkyl group of 1 to 5 carbon atoms, with the proviso that the carbon group directly attached to the benzylic carbon of each of the first and second groups is not a $CH_2$ group.

13. The process according to claim 12, wherein the alkylated hydroxyaromatic compound is a mixture of ortho and para isomers.

14. The process according, to claim 12, wherein the alkylated hydroxyaromatic compound comprises from about 1 to 99% ortho isomer and from about 99 to about 1% para isomer.

15. The process according to claim 12, wherein the alkylated hydroxyaromatic compound comprises from about 5 to about 70% ortho isomer and from about 95 to about 30% para isomer.

16. The process according to claim 12, wherein the at least one branched olefinic propylene oligomer has from about 20 to about 60 carbon atoms.

17. The process according to claim 12, wherein the at least one branched olefinic propylene oligomer is a mixture of branched olefinic propylene oligomers.

18. A process for alkylating a hydroxyaromatic compound comprising (a) oligomerizing propylene in the presence of an acidic ionic liquid catalyst to provide at least one branched olefinic propylene oligomer having from about 20 to about 80 carbon atoms, wherein the at least one branched olefinic propylene oligomer has less than about 1 wt. % of vinylidene content, and (b) reacting at least one hydroxyaromatic compound with the at least one branched olefinic propylene oligomer having from about 20 to about 80 carbon atoms in the presence of an acid catalyst to provide an alkylated hydroxyaromatic compound, wherein the benzylic carbon attached to the hydroxyaromatic ring is substituted with one group being methyl or a branched alkyl group of 3 to 5 carbon atoms, a second group being a branched alkyl group of at least about 18 carbon atoms having an average of one branch every 2 carbon atoms wherein each branch contains 1 to 2 carbon atoms, and a third group being a linear alkyl group of 1 to 5 carbon atoms, with the proviso that the carbon group directly attached to the benzylic carbon of each of the first and second groups is not a $CH_2$ group.

19. The process according to claim 18, wherein the acidic ionic liquid catalyst comprises a first component and a second component, the first component comprising to compound selected from the group consisting of aluminum halide, alkyl aluminum halide, gallium halide, and alkyl gallium halide, and the second component comprising a salt selected from an ammonium salt, a phosphonium salt, or a sulfonium salt.

20. The process according to claim 18, wherein the at least one branched olefinic propylene oligomer has from about 20 to about 60 carbon atoms.

21. The process according to claim 18, wherein the at least one branched olefinic propylene oligomer is a mixture of branched olefinic propylene oligomers.

* * * * *